United States Patent
Umezawa et al.

(10) Patent No.: US 7,214,856 B2
(45) Date of Patent: May 8, 2007

(54) PLANT HAVING TOLERANCE TO ENVIRONMENTAL STRESS

(75) Inventors: Taishi Umezawa, Ibaraki (JP); Kazuo Shinozaki, Ibaraki (JP)

(73) Assignee: Riken, Wako-shi (JP)

( * ) Notice: Subject to any disclaimer, the term of this patent is extended or adjusted under 35 U.S.C. 154(b) by 0 days.

(21) Appl. No.: 10/994,235

(22) Filed: Nov. 23, 2004

(65) Prior Publication Data

US 2005/0214808 A1 Sep. 29, 2005

(30) Foreign Application Priority Data

Mar. 12, 2004 (JP) ............................. 2004-071266

(51) Int. Cl.
*C12N 15/82* (2006.01)
*C12N 15/90* (2006.01)

(52) U.S. Cl. ................... 800/289; 800/293; 800/294

(58) Field of Classification Search ................ None
See application file for complete search history.

(56) References Cited

FOREIGN PATENT DOCUMENTS

EP          1033405 A2 * 9/2000

OTHER PUBLICATIONS

Keskin et al. (Protein Science, 13:1043-1055, 2004).*
Thornton et al. (Nature structural Biology, structural genomics supplement, Nov. 2000).*
Guo et al. (PNAS, 101: 9205-9210, 2004).*
Cheong et al. (Plant Physiol., 132:1961-1972, 2003).*
Umezawa et al. (PNAS, 101:17306-17311, 2004).*
Q. Liu et al., The Plant Cell, vol. 10, pp. 1391-1406, Aug. 1998.
M. Kasuga et al., Nature Biotechnology, vol. 17, pp. 287-291, Mar. 1999.
R. Yoshida et al., Plant Cell Physiol., vol. 43, No. 12, pp. 1473-1483, 2002.
T. Umezawa et al., The 26th Annual Meeting of the Molecular Biology Society of Japan, Program and Abstracts, 2PB-052, Dec. 2003.

* cited by examiner

*Primary Examiner*—Ashwin Mehta
*Assistant Examiner*—Vinod Kumar
(74) *Attorney, Agent, or Firm*—Oblon, Spivak, McClelland, Maier & Neustadt, P.C.

(57) ABSTRACT

A stress-tolerant transgenic plant comprising an exogenously-introduced polynucleotide encoding a protein kinase which activates stress-responsive transcription factors. The polynucleotide may encode a protein kinase which comprises SEQ ID NO: 2 (SRK-2C) or a sequence having a significant degree of similarity with SEQ ID NO: 2. The transgenic plant has increased stress-tolerance to environmental stresses, such as to dehydration, osmotic stress or low temperature stress, compared to a similar non-transgenic plant.

20 Claims, 5 Drawing Sheets
(2 of 5 Drawing Sheet(s) Filed in Color)

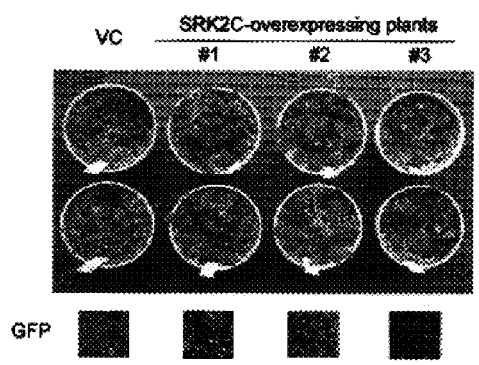
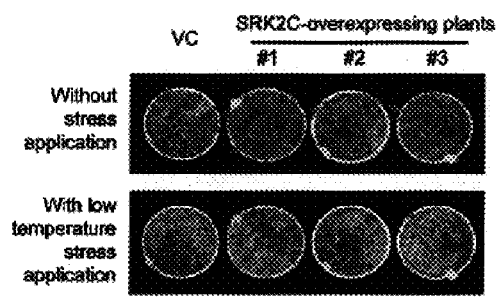
Fig. 3B
Fig. 3A
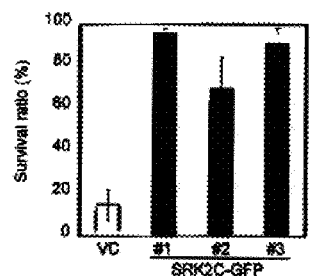
Fig. 3C
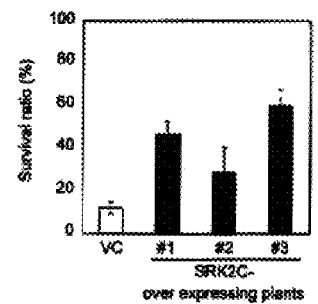
Fig. 3D

SEQUENCE LISTING

<160> NUMBER OF SEQ ID NOS: 4

<210> SEQ ID NO 1
<211> LENGTH: 1032
<212> TYPE: DNA
<213> ORGANISM: Arabidopsis
<220> FEATURE:
<221> NAME/KEY: CDS
<222> LOCATION: (1)..(1032)

<400> SEQUENCE: 1

```
atg gag agg tac gaa ata gtg aag gat att ggg tct ggt aac ttc gga       48
Met Glu Arg Tyr Glu Ile Val Lys Asp Ile Gly Ser Gly Asn Phe Gly
  1               5                  10                  15 gta gca aag ctt gtt cgt gac aaa ttt tcc aaa gag ctt ttc gct gtt       96
Val Ala Lys Leu Val Arg Asp Lys Phe Ser Lys Glu Leu Phe Ala Val
             20                  25                  30 aag ttc atc gag cga ggc caa aag att gat gaa cat gta caa aga gaa      144
Lys Phe Ile Glu Arg Gly Gln Lys Ile Asp Glu His Val Gln Arg Glu
         35                  40                  45 atc atg aac cat agg tcg ctg atc cat ccc aat ata ata aga ttc aag      192
Ile Met Asn His Arg Ser Leu Ile His Pro Asn Ile Ile Arg Phe Lys
     50                  55                  60 gag gtt tta ttg acg gca aca cat ttg gcg tta gta atg gaa tac gcc      240
Glu Val Leu Leu Thr Ala Thr His Leu Ala Leu Val Met Glu Tyr Ala
 65                  70                  75                  80 gcc gga gga gaa ctg ttc gga aga atc tgc agc gcc gga aga ttc agt      288
Ala Gly Gly Glu Leu Phe Gly Arg Ile Cys Ser Ala Gly Arg Phe Ser
                 85                  90                  95 gaa gac gag gca agg ttt ttc ttt cag cag ctt ata tca gga gtt aat      336
Glu Asp Glu Ala Arg Phe Phe Phe Gln Gln Leu Ile Ser Gly Val Asn
            100                 105                 110 tac tgt cac agt ctt caa ata tgc cat aga gat tta aag cta gag aac      384
Tyr Cys His Ser Leu Gln Ile Cys His Arg Asp Leu Lys Leu Glu Asn
        115                 120                 125 acg tta ctt gat gga agc gaa gcg cca cgt gta aag att tgc gac ttt      432
Thr Leu Leu Asp Gly Ser Glu Ala Pro Arg Val Lys Ile Cys Asp Phe
    130                 135                 140 gga tat tca aaa tca gga gtt ctt cat tcg caa cca aag aca aca gta      480
Gly Tyr Ser Lys Ser Gly Val Leu His Ser Gln Pro Lys Thr Thr Val
145                 150                 155                 160 gga aca cct gct tac att gca cct gaa gtg ctc tcc acg aaa gag tat      528
Gly Thr Pro Ala Tyr Ile Ala Pro Glu Val Leu Ser Thr Lys Glu Tyr
                165                 170                 175 gac ggc aaa atc gct gat gtt tgg tct tgt gga gtc act ttg tat gtt      576
Asp Gly Lys Ile Ala Asp Val Trp Ser Cys Gly Val Thr Leu Tyr Val
            180                 185                 190 atg ctt gtt ggt gct tat cct ttt gaa gat cct tct gat cct aaa gat      624
Met Leu Val Gly Ala Tyr Pro Phe Glu Asp Pro Ser Asp Pro Lys Asp
        195                 200                 205 ttt cgg aag acg atc ggt cgg att ctc aaa gct cag tat gct att cct      672
Phe Arg Lys Thr Ile Gly Arg Ile Leu Lys Ala Gln Tyr Ala Ile Pro
    210                 215                 220
```

-continued

```
gat tat gtt cga gtt tcg gat gaa tgc aga cat ctt ctc tct cgg ata    720
Asp Tyr Val Arg Val Ser Asp Glu Cys Arg His Leu Leu Ser Arg Ile
225                 230                 235                 240 ttc gtt gcc aac cct gaa aag aga ata aca ata gag gag ata aag aat    768
Phe Val Ala Asn Pro Glu Lys Arg Ile Thr Ile Glu Glu Ile Lys Asn
            245                 250                 255 cat tct tgg ttt ctc aag aac ttg ccg gta gag atg tat gaa gga tca    816
His Ser Trp Phe Leu Lys Asn Leu Pro Val Glu Met Tyr Glu Gly Ser
        260                 265                 270 ttg atg atg aat ggt cca tcg act cag aca gta gaa gag ata gtg tgg    864
Leu Met Met Asn Gly Pro Ser Thr Gln Thr Val Glu Glu Ile Val Trp
    275                 280                 285 atc att gaa gaa gct cgg aaa cct atc acc gta gct act gga ctc gca    912
Ile Ile Glu Glu Ala Arg Lys Pro Ile Thr Val Ala Thr Gly Leu Ala
290                 295                 300 ggt gct ggt ggc tct ggt gga agc agt aat ggt gcc att gga agt agc    960
Gly Ala Gly Gly Ser Gly Gly Ser Ser Asn Gly Ala Ile Gly Ser Ser
305                 310                 315                 320 agt atg gat ctc gat gac ttg gac aca gat ttc gac gac atc gat acc   1008
Ser Met Asp Leu Asp Asp Leu Asp Thr Asp Phe Asp Asp Ile Asp Thr
                325                 330                 335 gct gat ctc ctt tcc cct ttg tga                                   1032
Ala Asp Leu Leu Ser Pro Leu
            340
```

<210> SEQ ID NO 2
<211> LENGTH: 343
<212> TYPE: PRT
<213> ORGANISM: Arabidopsis

<400> SEQUENCE: 2

```
Met Glu Arg Tyr Glu Ile Val Lys Asp Ile Gly Ser Gly Asn Phe Gly
1               5                   10                  15

Val Ala Lys Leu Val Arg Asp Lys Phe Ser Lys Glu Leu Phe Ala Val
            20                  25                  30

Lys Phe Ile Glu Arg Gly Gln Lys Ile Asp Glu His Val Gln Arg Glu
        35                  40                  45

Ile Met Asn His Arg Ser Leu Ile His Pro Asn Ile Ile Arg Phe Lys
    50                  55                  60

Glu Val Leu Leu Thr Ala Thr His Leu Ala Leu Val Met Glu Tyr Ala
65                  70                  75                  80

Ala Gly Gly Glu Leu Phe Gly Arg Ile Cys Ser Ala Gly Arg Phe Ser
                85                  90                  95

Glu Asp Glu Ala Arg Phe Phe Phe Gln Gln Leu Ile Ser Gly Val Asn
            100                 105                 110

Tyr Cys His Ser Leu Gln Ile Cys His Arg Asp Leu Lys Leu Glu Asn
        115                 120                 125

Thr Leu Leu Asp Gly Ser Glu Ala Pro Arg Val Lys Ile Cys Asp Phe
    130                 135                 140

Gly Tyr Ser Lys Ser Gly Val Leu His Ser Gln Pro Lys Thr Thr Val
145                 150                 155                 160

Gly Thr Pro Ala Tyr Ile Ala Pro Glu Val Leu Ser Thr Lys Glu Tyr
                165                 170                 175

Asp Gly Lys Ile Ala Asp Val Trp Ser Cys Gly Val Thr Leu Tyr Val
            180                 185                 190

Met Leu Val Gly Ala Tyr Pro Phe Glu Asp Pro Ser Asp Pro Lys Asp
        195                 200                 205
```

```
Phe Arg Lys Thr Ile Gly Arg Ile Leu Lys Ala Gln Tyr Ala Ile Pro
    210                 215                 220

Asp Tyr Val Arg Val Ser Asp Glu Cys Arg His Leu Leu Ser Arg Ile
225                 230                 235                 240

Phe Val Ala Asn Pro Glu Lys Arg Ile Thr Ile Glu Glu Ile Lys Asn
                245                 250                 255

His Ser Trp Phe Leu Lys Asn Leu Pro Val Glu Met Tyr Glu Gly Ser
            260                 265                 270

Leu Met Met Asn Gly Pro Ser Thr Gln Thr Val Glu Glu Ile Val Trp
        275                 280                 285

Ile Ile Glu Glu Ala Arg Lys Pro Ile Thr Val Ala Thr Gly Leu Ala
    290                 295                 300

Gly Ala Gly Gly Ser Gly Gly Ser Ser Asn Gly Ala Ile Gly Ser Ser
305                 310                 315                 320

Ser Met Asp Leu Asp Asp Leu Asp Thr Asp Phe Asp Asp Ile Asp Thr
                325                 330                 335

Ala Asp Leu Leu Ser Pro Leu
            340

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 3
tctagaatgg agaggtacga aatag                                          25

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 4
ggatcccaaa ggggaaagga gatcag                                         26
```

PLANT HAVING TOLERANCE TO ENVIRONMENTAL STRESS

TECHNICAL FIELD

The present invention relates to a gene encoding protein kinase capable of activating transcription of a gene group under the control of a stress-responsive transcription factor by inducing the expression thereof and a transgenic plant having such gene introduced therein and having high tolerance to environmental stresses.

BACKGROUND ART

Plant growth is considerably influenced by environmental factors such as dehydration, salt, or low temperature. This is directly correlated to the issue of agricultural production, and development of crops having environmental stress tolerance has been awaited as a technique of improving agricultural production efficiency around the world. From such a point of view, development of a variety of environmental stress tolerant plants was achieved with the utilization of a classical breeding method and biotechnology such as gene recombination. In the case of plants to which enzyme genes that synthesize an amino acid (proline) or an oligosaccharide (galactinol) have been introduced, for example, proline or galactinol imparts the osmoregulatory mechanism to such plants. Accordingly, such plants gain tolerance to dehydration or salt stress. A method for imparting stress tolerance to plants via overexpression of a single gene therein is effective to some extent. However, such method is often disadvantageous for plants because it affects plant growth or because the effects attained thereby are insignificant. Many plants actually possess genes that can impart environmental stress tolerance as mentioned above, and such genes actively function to acquire tolerance when the plants receive stresses. Since these genes are considered to express upon reception of instructions from a given upstream factor, all the downstream genes are regulated and stress tolerance can be enhanced if such upstream factor can be identified. Such perspective is referred to as "regulon biotechnology" and has drawn attention in recent days. An example of the upstream factor that regulates gene expression is a "transcription factor" that directly regulates transcription of messenger RNA. Recently, DREB/CBF was identified as a transcription factor associated with dehydration and low temperature stresses. The transgenic plants thereof were found to have activated expression of downstream genes and have tolerance to dehydration, salt, or low temperature stress (Quiang Liu et al., The Plant Cell, vol. 10, 1391–1406, 1998; Mie Kasuga et al., Nature Biotechnology, vol. 17, 287–291, 1999). However, no signal transduction factor that would activate the DREB/CBF transcription factor has been found in the upstream region. Accordingly, elucidation of the upstream signal transduction factor associated with such environmental responses is considered to be useful for the development of plants having enhanced stress tolerance.

Abscisic acid (ABA) is a plant hormone associated with seed dormancy, stomatal opening and closing, and osmotic stress tolerance. ABA is deeply involved in the expression of the stress responsive gene group. When a plant receives stress such as dehydration, signal transduction takes place via the ABA-dependent path and the ABA-independent path, and this signal transduction is known to regulate the expression of the stress responsive gene group. It is reported that ABA signal transduction is involved in a wide variety of factors, and protein kinase is one of them. The present inventors have focused on the correlation between the ABA signal transduction system and protein phosphorylation, identified the SnRK2 (SNF1-related protein kinase 2) family as the protein kinase group that is specifically activated by ABA, and demonstrated that a member thereof, i.e., SRK2E, regulates stomatal opening and closing and is involved in the expression of ABA inducible genes (Riichiro Yoshida et al., Plant Cell Physiol., 43 (12), 1473–1483, 2002).

DISCLOSURE OF THE INVENTION

Accordingly, the objects of the present invention are to elucidate the signal transduction factor located upstream of the gene group associated with environmental responses and to provide a transgenic plant having stress tolerances via the utilization of such factor.

The present inventors have conducted concentrated studies in order to attain the above objects. As a result, they have found that overexpression of the SRK2C gene that is a member of the SnRK2 protein kinase family via introduction thereof into a plant results in an increased expression level of the DREB/CBF transcription factors and in the exhibition of high tolerance to dehydration, osmotic, or low temperature stress. The present invention has been completed based on such findings.

Specifically, the present invention includes the following.

(1) A gene encoding the following protein (a) or (b):
(a) a protein consisting of the amino acid sequence as shown in SEQ ID NO: 2 in the Sequence Listing; or
(b) a protein consisting of an amino acid sequence derived from the amino acid sequence as shown in SEQ ID NO: 2 in the Sequence Listing by deletion, substitution, or addition of one or several amino acid residues and having activity of inducing expression of stress responsive transcription factors and activity of protein kinase.

(2) A gene consisting of the following DNA (c) or (d):
(c) DNA consisting of the nucleotide sequence as shown in SEQ ID NO: 1 in the Sequence Listing; or
(d) DNA hybridizing under stringent conditions to DNA consisting of a nucleotide sequence complementary to DNA consisting of the nucleotide sequence as shown in SEQ ID NO: 1 in the Sequence Listing and encoding a protein having activity of inducing expression of stress responsive transcription factors and activity of protein kinase.

(3) The gene according to (1) or (2), wherein the stress responsive transcription factor is DREB/CBF.

(4) A protein (a) or (b):
(a) a protein consisting of the amino acid sequence as shown in SEQ ID NO: 2; or
(b) a protein consisting of an amino acid sequence derived from the amino acid sequence as shown in SEQ ID NO: 2 by deletion, substitution, or addition of one or several amino acid residues and having activity of inducing expression of stress responsive transcription factors and activity of protein kinase.

(5) A recombinant vector comprising the gene according to any of (1) to (3).

(6) A stress tolerant transgenic plant having the gene according to any of (1) to (3) or the recombinant vector according to (5) introduced therein.

(7) The stress tolerant transgenic plant according to (6), which is a plant body, a plant organ, a plant tissue, or a cultured plant cell.

(8) The stress tolerant transgenic plant according to (6) or (7), wherein the type of stress is at least one type selected from the group consisting of dehydration, osmotic, and low temperature stresses.

(9) The stress tolerant transgenic plant according to any of (6) to (8), which belongs to any of the families selected from the group consisting of *Gramineae, Liliaceae, Zingiberaceae, Brassicaceae, Solanaceae, Leguminosae, Cucurbitaceae, Umbelliferae, Asteraceae, Malvaceae, Chenopodiaceae, Myrtaceae*, and *Salicaceae*.

(10) A method for imparting stress tolerance to plants, wherein the genes according to any of (1) to (3) are overexpressed in plants.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A shows the results of a dehydration stress tolerance test of the SRK2C-overexpressing plants (photograph: plants of each line (2 pots) after the application of dehydration stress; FIG. 3C graph: the survival ratio of plants of each line after the application of dehydration stress).

FIG. 3B shows the results of a freezing-tolerance test of the SRK2C-overexpressing plants (the upper photograph: plants of each line without the application of low temperature stress; the lower photograph: plants of each line after the application of low temperature stress;

FIG. 3D graph: the survival ratio of plants of each line after the application of low temperature stress).

Figure 1A:
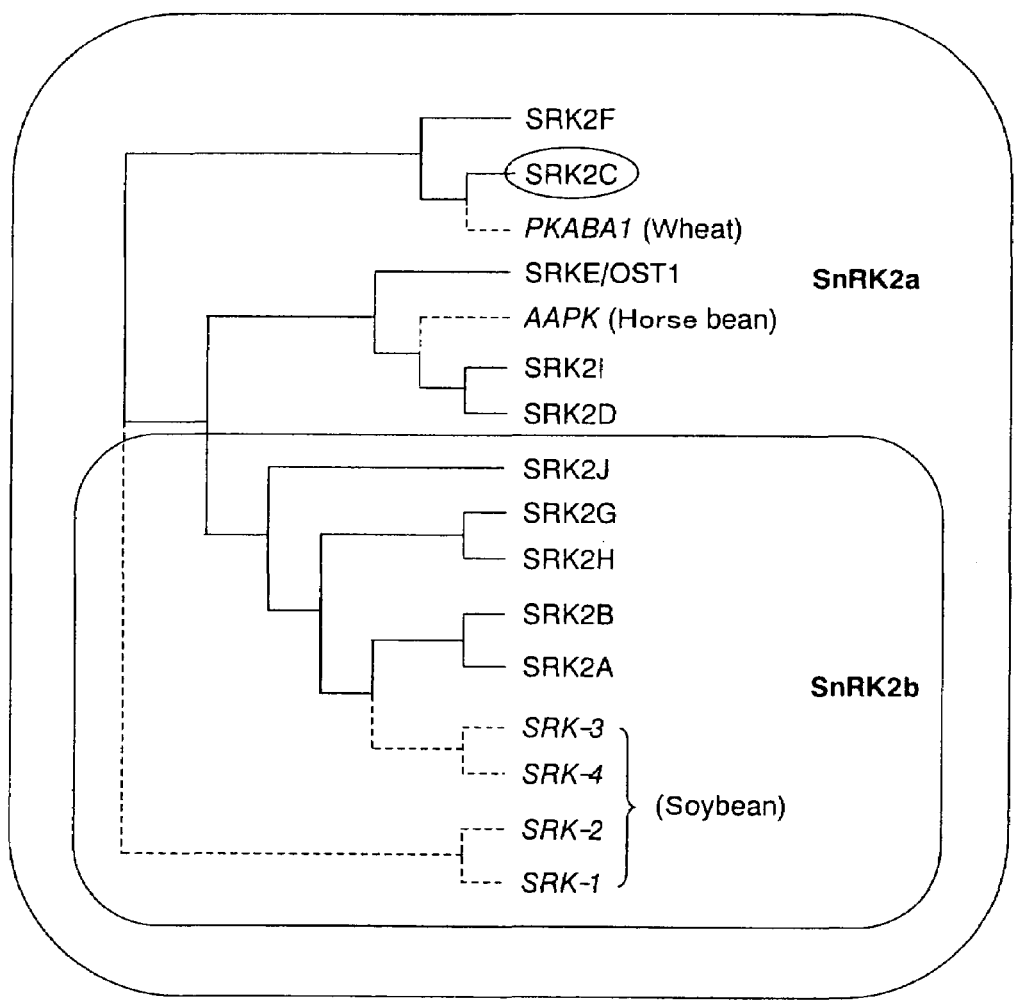
FIG. 1A shows the SnRK2 protein kinase family.
Figure 1B:
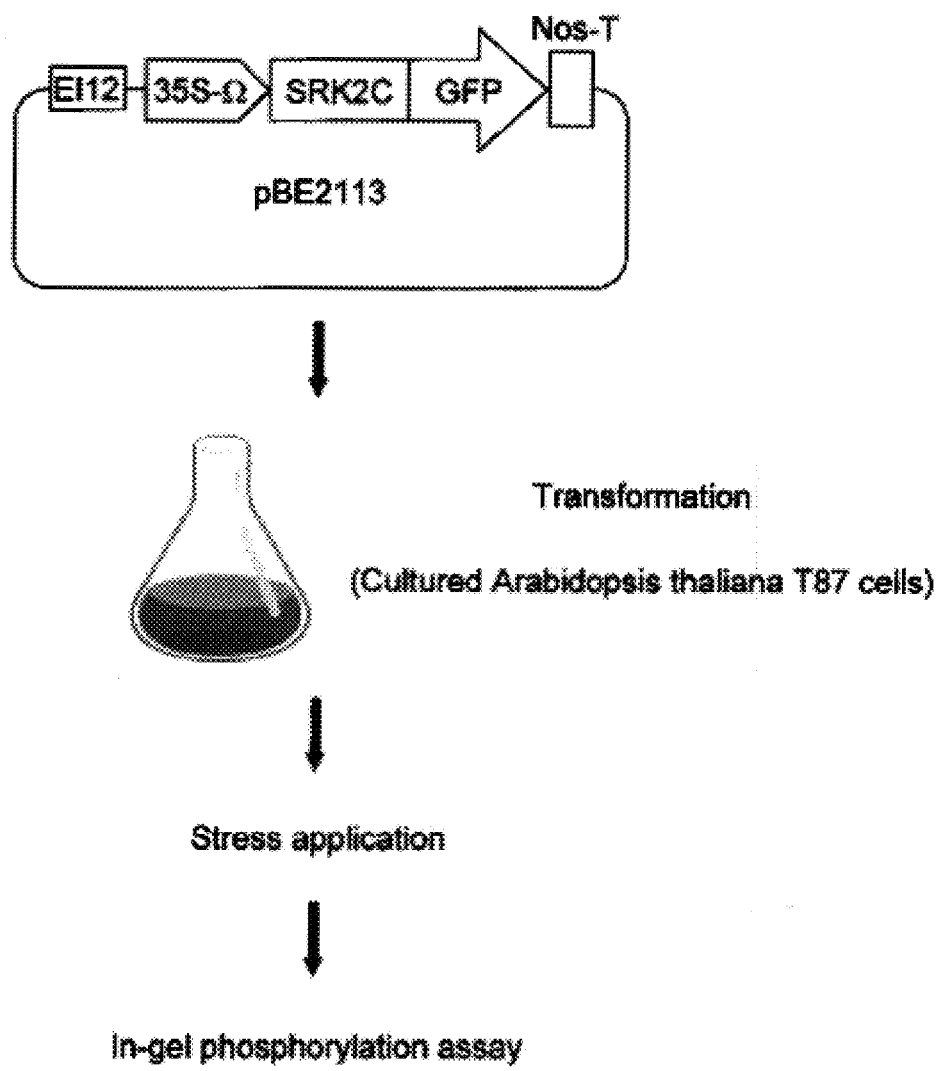
FIG. 1B shows the scheme of the method for analyzing SRK2C functions in plants.

Hereafter, the present invention is described in detail. This patent application claims priority from Japanese Patent Application No. 2004-071266 filed on Mar. 12, 2004, and includes part or all of the contents as disclosed in the description thereof.

1. Gene Cloning

The gene according to the present invention encodes a signal transduction factor that induces the expression of a transcription factor that binds to a cis-element located upstream of a gene encoding a stress-responsive protein expressed by environmental stresses such as dehydration, osmotic pressure, and low temperature stresses and activates the transcription thereof (hereafter referred to as "stress responsive transcription factor"). An example of the "stress responsive transcription factor" is one that binds to a dehydration-responsive element (DRE) and activates the transcription of the gene located downstream of the stress-responsive element. A specific example thereof is the DREB/CBF transcription factor.

The gene according to the present invention is cloned, for example, in the following manner.

(1) Preparation of mRNA and cDNA Library of *Arabidopsis thaliana*

A source of mRNA may be a part of a plant such as leaves, stems, roots, or flowers of *Arabidopsis thaliana* or the whole plant. Alternatively, a plant obtained by sowing *Arabidopsis thaliana* seeds on a solid medium such as GM medium, MS medium, or #3 medium and growing them aseptically can be used. The mRNA level of the gene according to the present invention in the *Arabidopsis thaliana* plants increases upon exposure of the plants to osmotic (salt) stress (e.g., 50 mM to 600 mM NaCl) or low temperature stress (e.g., $-10°$ C. to $10°$ C.). Accordingly, *Arabidopsis thaliana* plants that have been exposed to such stress may be used.

mRNA is prepared by, for example, exposing the *Arabidopsis thaliana* plants that had been grown in GM medium to dehydration, osmotic (salt), or low temperature stress and freezing the resultant with liquid nitrogen, followed by a conventional technique. For example, the frozen plants are ground in a mortar, etc., and a crude RNA fraction is extracted therefrom by the glyoxal method, the guanidine thiocyanate and cesium chloride method, the lithium chloride and urea method, or the proteinase K and deoxyribonuclease method. RNA may be extracted using a commercially available kit (Total RNA Extraction Kit, Amersham).

The thus obtained crude RNA fraction is used as a template to synthesize single-stranded cDNA using an oligo dT primer and reverse transcriptase. Thereafter, the single-stranded cDNA is used as a template to conduct RT-PCR using a primer that was prepared to amplify the coding region (AGI code: Atlg78290) based on the genomic information of *Arabidopsis thaliana*. Thus, cDNA of SRK2C is amplified.

The nucleotide sequence of the cDNA of the obtained clone of interest is determined. The nucleotide sequence can be determined via conventional techniques such as the chemical modification technique of Maxam-Gilbert or the dideoxynucleotide chain termination method utilizing M13 phage. In general, sequencing is carried out using an automated nucleotide sequencer (e.g., the ABI373 Sequencer and the 310 DNA Sequencer, Applied Biosystems). The determined nucleotide sequence is analyzed using DNA analyzing software such as DNASIS (Hitachi Software Engineering Co., Ltd), and a protein-encoding region that is encoded in the obtained DNA strand can be found.

The nucleotide sequence of the gene according to the present invention is shown in SEQ ID NO: 1 and the amino acid sequence of the protein encoded by the gene according to the present invention is shown in SEQ ID NO: 2.

Amino acid sequences can differ to some extent between plants due to the varieties thereof or the like. Also, amino acid sequences may vary due to mutation or other reasons even between plants of the same species.

Accordingly, the gene according to the present invention includes a gene consisting of an amino acid sequence derived from the amino acid sequence as shown in SEQ ID NO: 2 by deletion, substitution, or addition of one or several amino acids and encoding a protein having activity of inducing the expression of stress responsive transcription factors and activity of protein kinase.

The number of the amino acid residues that may be deleted, substituted, or added is preferably 1 to several. For example, 1 to 10, and preferably 1 to 5, amino acid residues may be deleted from the amino acid sequence as shown in SEQ ID NO: 2; 1 to 10, and preferably 1 to 5, amino acid residues may be added to the amino acid sequence as shown in SEQ ID NO: 2; or 1 to 10, and preferably 1 to 5, amino acid residues may be substituted with other amino acid residues in the amino acid sequence as shown in SEQ ID NO: 2.

The gene according to the present invention includes a gene that exhibits 70% or higher homology to the amino acid sequence as shown in SEQ ID NO: 2 and that encodes a protein having activity of inducing the expression of stress responsive transcription factors and activity of protein kinase.

The aforementioned 70% or higher homology preferably refers to homology of 80% or higher, more preferably to homology of 90% or higher, and most preferably to homology of 95% or higher.

The term "activity of inducing the expression of stress responsive transcription factors" refers to the activity of enhancing the expression of stress responsive transcription factors such as DREB/CBF.

The term "activity of protein kinase" refers to the activity of phosphorylating a specific amino acid residue that constitutes a protein. The activity of protein kinase can be confirmed by, for example, subjecting a protein extract that has been prepared from leaves of a transgenic plant to an in-gel phosphorylation assay that employs histone as a substrate (Riichiro Yoshida et al., Plant Cell Physiol., 43 (12), 1473–1483, 2002). When a spot is observed at a molecular weight of 35 kDa to 75 kDa via SDS-PAGE (gel concentration of 8%), it can be evaluated as being "active."

The phrase "having activity of inducing the expression of stress responsive transcription factors and activity of protein kinase" refers to the fact that such two activities are substantially the same as the activity of a protein that has the amino acid sequence as shown in SEQ ID NO: 2.

The gene according to the present invention also includes DNA that hybridizes under stringent conditions to DNA consisting of the nucleotide sequence complementary to DNA consisting of the nucleotide sequence as shown in SEQ ID NO: 1 in the Sequence Listing and that encodes a protein having activity of inducing the expression of stress responsive transcription factors and activity of protein kinase.

The term "stringent conditions" refers to conditions where what is called a specific hybrid is formed but a non-specific hybrid is not formed. For example, under such conditions, complementary strands of DNA consisting of a highly homologous nucleic acid, i.e., DNA consisting of a nucleotide sequence exhibiting 70% or higher, preferably 80% or higher, more preferably 90% or higher, and most preferably 95% or higher homology to the nucleotide sequence as shown in SEQ ID NO: 1 hybridize, but complementary strands of a nucleic acid having homology lower than the aforementioned level does not hybridize. More specific conditions are constituted by a sodium concentration of 150 mM to 900 mM, and preferably 600 mM to 900 mM, and a temperature of 60° C. to 68° C., and preferably 65° C.

The aforementioned deletion, addition, and substitution of amino acid residues can be carried out by modifying the aforementioned protein-encoding gene via a technique known in the art. Mutation can be introduced to a gene via conventional techniques such as the Kunkel method or the Gapped duplex method, or via a technique in accordance therewith. For example, mutation is introduced using a mutagenesis kit, such as a Mutant-K (Takara) or Mutant-G (Takara) utilizing site-directed mutagenesis or the Takara LA PCR in vitro Mutagenesis series kit (Takara).

Once the nucleotide sequence of the gene according to the present invention is determined, the gene according to the present invention can be then obtained via chemical synthesis, PCR utilizing cDNA or genomic DNA of the gene according to the present invention as a template, or hybridization utilizing a DNA fragment having such nucleotide sequence as a probe.

2. Preparation of Recombinant Vector and Transgenic Plant (1) Preparation of Recombinant Vector The recombinant vector according to the present invention can be constructed by introducing the gene described in 1. above (hereafter, it may be referred to as "the target gene") into an adequate vector. For example, pBI, pPZP, and pSMA vectors that can introduce the target gene into a plant via Agrobacterium are preferably used. A pBI binary vector or intermediate vector is particularly preferable and examples thereof include pBI121, pBI101, pBI110.2, and pBI101.3. A binary vector is a shuttle vector that can be replicated in E. coli and in Agrobacterium. When Agrobacterium containing a binary vector is allowed to infect plants, DNA in the portion sandwiched between border sequences consisting of the LB sequence and the RB sequence on the vector can be incorporated into the plant nuclear DNA (EMBO Journal, 10 (3), 697–704, 1991). In contrast, a pUC vector can directly introduce a gene into plants. Examples thereof include pUC18, pUC19, and pUC9 vectors. Plant virus vectors, such as cauliflower mosaic virus (CaMV), bean golden mosaic virus (BGMV), and tobacco mosaic virus (TMV) vectors, can also be used.

When a binary vector plasmid is used, the target gene is inserted between the border sequences (LB and RB sequences) of the binary vector, and this recombinant vector is then amplified in E. coli. Subsequently, the amplified recombinant vector is introduced into Agrobacterium tumefaciens C58, LBA4404, EHA101, EHA105, or the like via electroporation or other means, and the aforementioned Agrobacterium is used for genetic transduction of plants.

The target gene is inserted into the vector by first cleaving the purified DNA with an adequate restriction enzyme, inserting the cleavage fragment into the restriction site or multicloning site of an adequate vector DNA, and ligating the product to the vector.

The target gene needs to be incorporated into a vector in a manner such that functions of the gene are exhibited. A promoter, an enhancer, a terminator, a poly A additional signal, a 5'-UTR sequence, a selection marker gene, or the like can be ligated to the vector at a site upstream, inside, or downstream of the gene described in 1. above.

It is possible that the "promoter" not be derived from plants as long as the DNA can function in plant cells and can induce expression in a specific plant tissue or during a specific growth phase. Specific examples thereof include a cauliflower mosaic virus (CaMV) 35S promoter, a nopalin synthase gene promoter (Pnos), a maize ubiquitin promoter, a rice actin promoter, and a tobacco PR protein promoter.

An example of an enhancer is an enhancer region that is used for improving the expression efficiency of the target gene and that comprises the upstream sequence in the CaMV 35S promoter.

Any terminator can be used as long as it can terminate transcription of the gene transcribed by a promoter. Examples thereof include a nopalin synthase (NOS) gene terminator, an octopine synthase (OCS) gene terminator, and a CaMV 35S RNA gene terminator.

Examples of a selection marker gene include an ampicillin resistant gene, a neomycin resistant gene, a hygromycin resistant gene, and a bialaphos resistant gene.

The selection marker gene and the target gene may be ligated to the same plasmid to prepare a recombinant vector. Alternatively, a recombinant vector that is obtained by ligating the selection marker gene to a plasmid may be prepared separately from a recombinant vector that is obtained by ligating the target gene to a plasmid. When recombinant vectors are separately prepared, both vectors are cotransfected into a host.

(2) Preparation of Transgenic Plant

The transgenic plant according to the present invention can be prepared by transforming the target plant using the recombinant vector described in (1) above.

Transgenic plants can be adequately prepared via a variety of reported and established techniques. Preferable examples thereof include the *Agrobacterium* method, the PEG-calcium phosphate method, electroporation, the liposome method, the particle gun method, and microinjection. The *Agrobacterium* method may employ a protoplast, a tissue section, or a plant itself (the in planta method). When a protoplast is employed, the protoplast is cultured together with the *Agrobacterium* having a Ti plasmid, or it is fused with a spheroplasted *Agrobacterium* (the spheroplast method). When a tissue section is employed, *Agrobacterium* is allowed to infect a leaf section (a leaf disc) of an aseptically cultivated target plant or a callus. When the in planta method that utilizes seeds or plants is employed, i.e., a method that is not carried out via tissue culture with the addition of plant hormones, *Agrobacterium* can be directly applied to water absorptive seeds, seedlings, potted plants, and the like.

When a gene is introduced via *Agrobacterium* infection, a step of allowing *Agrobacterium* that has a plasmid containing the target gene to infect plants is required. This can be carried out via vacuum infiltration. More specifically, *Arabidopsis thaliana* that had been grown in soil containing vermiculite and an equivalent amount of perlite is directly soaked in a culture solution of *Agrobacterium* containing a plasmid that contains the target gene. The product is placed in a decicator, suctioned with a vacuum pump to 65 to 70 mmHg, and then allowed to stand at room temperature for 5 to 10 minutes. The pot is transferred onto a tray, covered with a wrap, and kept moistened. The wrap is removed on the following day, the plant is allowed to grow in that state, and seeds are then harvested. Subsequently, seeds are sown on MS agar medium to which adequate antibiotics have been added in order to select an individual having the target gene. *Arabidopsis thaliana* that has been grown in this medium is transferred to a pot and allowed to grow therein. Thus, seeds of transgenic plants to which the target gene has been incorporated can be obtained.

Whether or not the gene has been incorporated into the plant can be confirmed via PCR, Southern hybridization, Northern hybridization, Western blotting, or other means. For example, DNA is prepared from a transgenic plant, a DNA-specific primer is designed, and PCR is then carried out. After PCR has been carried out, the amplification product is subjected to agarose gel electrophoresis, polyacrylamide gel electrophoresis, or capillary electrophoresis and stained with ethidium bromide, a SYBR Green solution, or the like, thereby detecting the amplification product as a band. Thus, transformation can be confirmed. Alternatively, the amplification product can be detected via PCR with the use of a primer that has been previously labeled with a fluorescent dye or the like. Further, the amplification product may be bound to a solid phase such as a microplate to thereby confirm the amplification product via fluorescent or enzyme reactions.

Alternatively, a variety of reporter genes such as β-glucuronidase (GUS), luciferase (LUC), green fluorescent protein (GFP), chloramphenicol acetyltransferase (CAT), or β-galactosidase (LacZ) are ligated to the downstream region of the target gene to prepare a vector. *Agrobacterium* to which the aforementioned vector has been incorporated is used to transform a plant in the same manner as described above, and the expression of the reporter gene is assayed. Thus, incorporation of the gene into the plant can be confirmed.

In the present invention, monocotyledonous plants or dicotyledonous plants may be used for transformation. Examples of monocotyledonous plants include those belonging to: *Gramineae* such as rice, barley, wheat, maize, sugar cane, *Zoysia*, sorghum, Italian millet, and Japanese millet; *Liliaceae* such as asparagus, lily, onion, *Allium tuberosum*, and Japanese dog's tooth violet; and *Zingiberaceae* such as ginger, *Zingiber mioga*, and *Curcuma longa*. Examples of dicotyledonous plants include, but are not limited to, those belonging to: *Brassicaceae* such as *Arabidopsis thaliana*, cabbage, rapeseed, cauliflower, broccoli, and radish; *Solanaceae* such as tomato, eggplant, potato, and tobacco; *Leguminosae* such as soybean, garden pea, bush bean, and alfalfa; *Cucurbitaceae* such as cucumber, melon, and pumpkin; *Umbelliferae* such as carrot, celery, and *Cryptotaenia japonica*; *Asteraceae* such as lettuce; *Malvaceae* such as *Gossypium nanking* and okra; *Chenopodiaceae* such as sugar beet and spinach; *Myrtaceae* such as Eucalyptus and clove; and *Salicaceae* such as poplar. Among them, plants belonging to the *Brassicaceae*, such as tobacco, soybean, or wheat, are particularly preferable.

In the present invention, examples of plant materials to be transformed include: plant tissues such as a root, stem, leaf, seed, embryo, ovule, ovary, shoot apex (the growing point at the edge of a plant seedling), anther, and pollen; sections of such plant tissues; undifferentiated calluses; and cultured plant cells such as protoplasts prepared by removing cell walls via enzyme processing. When the in planta method is employed, water absorptive seeds or a whole plant can also be used.

A transgenic plant in the present invention refers to a whole plant, a plant organ (such as a root, stem, leaf, petal, seed, or fruit), a plant tissue (such as the epidermis, phloem, parenchyma, xylem, or vascular bundle), or a cultured plant cell.

When a cultured plant cell is to be transformed, an organ or individual may be regenerated from the obtained transformed cell via conventional tissue culture techniques. A person skilled in the art can easily carry out such procedures via a common technique that is known as a method of regenerating a plant from a plant cell. For example, a plant can be regenerated from a plant cell in the following manner.

At the outset, when plant tissues or protoplasts are used as plant materials to be transformed, they are cultured in a callus-forming medium that has been sterilized with the addition of, for example, inorganic elements, vitamins, carbon sources, saccharides as energy sources, or plant growth regulators (plant hormones, such as auxin or cytokinin), and indeterminately proliferating dedifferentiated calluses are allowed to form (hereafter, this process is referred to as "callus induction"). The thus formed calluses are transferred to a new medium containing plant growth regulators, such as auxin, and then further proliferated (subculture).

Callus induction is carried out in a solid medium such as agar, and subculture is carried out in, for example, a liquid medium. This enables both cultures to be carried out efficiently and in large quantities. Subsequently, the calluses proliferated via the aforementioned subculture are cultured under adequate conditions to induce redifferentiation of organs (hereafter referred to as "induction of redifferentiation"), and a complete plant is finally regenerated. Induction of redifferentiation can be carried out by adequately determining the type and quantity of each ingredient in the medium, such as plant growth regulators such as auxin or cytokinin, and carbon sources, light, temperature, and other conditions. Such induction of redifferentiation results in formation of adventitious embryos, adventitious roots, adventitious buds, adventitious shoots, and the like, which leads to growth into complete plants. Alternatively, such items may be stored in a state that pertains before they become complete plants (e.g., encapsulated artificial seeds, dry embryos, or freeze-dried cells and tissues).

The transgenic plants according to the present invention include plants of the "T1 generation," that is, the redifferentiated generation that had been subjected to transformation; plants of the "T2 generation," that is, the progeny obtained from the seeds of the T1 generation; and progeny plants such as those of the next generation (T3 generation) obtained by self-pollination of flowers of the "T2 generation" plants that had been found to be transgenic via drug selection, Southern blotting, or other analyses.

A transgenic plant obtained in such a manner attains tolerance to environmental stress. Accordingly, the transgenic plant can be used as an environmental stress tolerant plant. The term "environmental stress" used herein generally refers to abiotic stress. Examples thereof include dehydration stress, osmotic stress, and low temperature stress. One or several types of such stresses may be applied.

The term "dehydration stress" refers to stress that is caused when a plant is persistently exposed to dehydrated conditions. The term "osmotic stress" refers to stress caused when the water potential is lowered and a substance that blocks moisture absorption is persistently applied. Examples of such substances include ionic substances (e.g., NaCl and $CaCl_2$) and nonionic substances (e.g., polyethylene glycol and mannitol). A representative example of osmotic stress is "salt stress" caused by application of NaCl having a high salt concentration. For example, "salt stress" is caused when 50 mM to 600 mM NaCl has been continuously applied over a period of 1 hour to several weeks.

"Low temperature stress" is generated upon persistent exposure to a temperature lower than the optimal temperature for a given species (e.g., when *Arabidopsis thaliana* is continuously exposed to temperatures of −10° C. to 5° C. over a period of 1 hour to several weeks).

3. Change in mRNA Levels of Various Genes in Transgenic Plants

Genes, the expression levels of which are considered to vary due to the action of the gene according to the present invention in a transgenic plant, can be identified via Northern blot analysis. Northern blot analysis can be carried out by comparing gene expression upon application of environmental stress between a transgenic plant to which the gene of the present invention has been introduced and a plant to which the same has not been introduced.

For example, environmental stress (dehydration, osmotic, or low temperature stress) is applied to plants that have been grown in GM agar medium or the like for a given period of time.

Dehydration stress is applied by, for example, suspending water supply for 1 to 2 weeks or removing a whole plant from soil or a water culture medium and exposing it to air for a given period of time. Osmotic stress is applied by, for example, adding sodium chloride to a concentration of 50 mM to 600 mM to a given water culture medium, cultivating a plant for 1 hour to several weeks, or adding polyethylene glycol (50 g/l to 200 g/l) to a water culture medium, medium, or the like. Low temperature stress is applied by, for example, allowing a plant to stand at temperatures of −10° C. to 5° C. for 10 minutes to 24 hours.

One or several types of environmental stresses may be applied.

Total RNA is prepared from a stress-free control plant and from a stress-applied plant, electrophoresis is carried out, and the genes that have been expressed are assayed via Northern blotting or RT-PCR.

4. Evaluation of Tolerance to Environmental Stress of Transgenic Plant

Tolerance to environmental stress of the transgenic plant according to the present invention can be evaluated by planting the transgenic plant in a pot containing soil including vermiculite, pearlite, and the like and inspecting the conditions of the plant (e.g., the growth rate, the survival ratio, the plant length, the weight, the yield, or a combination thereof) upon application of various types of stresses such as dehydration, osmotic, and low temperature stresses. Such stresses can be applied in the manner described above.

The term "tolerance to environmental stress" refers to the capacity for survival even upon application of the aforementioned environmental stress while the plant growth remains uninhibited.

5. Production of the Protein of the Invention

The protein of the present invention can be obtained by ligating (inserting) the gene of the present invention isolated in 1. above into a recombinant vector that can be replicated in a host such as plasmid DNA or phage DNA, introducing the vector into a host other than a plant host such as *E. coli* to obtain a transgenic plant, culturing the transgenic plant, and collecting the protein from the culture product. The "culture product" used herein refers to a culture supernatant, a cultured cell or microorganism, or a crushed product of the cultured cell or microorganism.

Examples of the aforementioned plasmid DNA include a plasmid derived from *E. coli* (e.g. pBR322, pBR325, pUC118, pUC119, pUC18, pUC19 and pBluescript), a plasmid derived from *Bacillus subtilis* (e.g. pUB110 and pTP5), and a plasmid derived from yeast (e.g. YEp13 and YCp50). Examples of phage DNA include the λ phage (e.g. Charon4A, Charon21A, EMBL3, EMBL4, λgt10, λgt11 and λZAP). Further, animal virus vectors such as a retrovirus and a vaccinia virus and insect virus vectors such as a baculovirus can also be used.

Examples of hosts other than plant hosts that can be employed include: bacteria belonging to *Escherichia* such as *E. coli*, *Bacillus* such as *Bacillus subtilis*, *Pseudomonas* such as *Pseudomonas putida*, and *Rhizobium* such as *Rhizobium meliloti*; yeast such as *Saccharomyces cerevisiae* and *Schizosaccharomyces pombe*; animal cells such as COS cell and CHO cell; and insect cells such as Sf9 cell.

Where a bacterium such as *E. coli* or yeast is used as a host, it is preferable that the aforementioned recombinant vector be capable of self-replicating in the bacterium and, at the same time, be also comprised of a promoter, a ribosome binding sequence, the gene of the present invention, and a transcription termination sequence. Further, it may also comprise a gene for regulating a promoter.

Examples of *E. coli* include *E. coli* DH5α and HB101 and examples of *Bacillus subtilis* include *Bacillus subtilis*, although they are not limited thereto. In such a case, a promoter is not particularly limited as long as it can express the gene of the present invention in a host such as *E. coli*. For example, *E. coli*-derived or phage-derived promoters can be employed, such as trp promoter, lac promoter, $P_L$ promoter, and $P_R$ promoter. A method for introducing a recombinant vector into a bacterium is not particularly limited, as long as it allows the introduction of DNA into a bacterium. For example, a method involving the use of calcium ions (Cohen, S. N. et al., Ploc. Natl. Acad. Sci., U.S.A., 69: 2110, 1972) and electroporation can be employed.

Where yeast is used as a host, for example, *Saccharomyces cerevisiae* or *Pichea pastris* is used. In this case, a promoter is not particularly limited as long as it can express the gene of the present invention in yeast. For example, gal1 promoter, gal10 promoter, heat shock protein promoter, MFαI promoter, PHO5 promoter, PGK promoter, GAP promoter, ADH promoter, or AOX1 promoter can be employed. A method for introducing a recombinant vector into yeast is not particularly limited, as long as it allows the introduction of DNA into yeast, and examples of such methods include electroporation, the spheroplast method, and the lithium phosphate method.

Where an animal cell is used as a host, a monkey COS-7 cell, Vero, a Chinese hamster ovary cell (a CHO cell), a mouse L cell, or the like are employed. In such a case, SRα promoter, SV 40 promoter, LTR promoter, CMV promoter, or the like is employed, and an early gene promoter of human cytomegalovirus may be employed. Examples of methods for introducing a recombinant vector into an animal cell include electroporation, the calcium phosphate method, and lipofection.

Where an insect cell is used as a host, an Sf9 cell or the like can be used. Examples of methods for introducing a recombinant vector into an insect cell include the calcium phosphate method, lipofection, and the electroporation method.

The aforementioned methods for culturing the transgenic plant are carried out in accordance with a conventional technique for culturing a host.

As a medium for culturing the transgenic plant obtained from a microorganism host such as *E. coli* or yeast, either a natural or synthetic medium may be used as long as it contains carbon sources, nitrogen sources, and inorganic salts assimilable by the microorganism and is capable of efficiently culturing the transgenic plant. Examples of carbon sources include: carbohydrates such as glucose, fructose, sucrose, and starch; organic acids such as acetic acid and propionic acid; and alcohols such as ethanol and propanol. Examples of nitrogen sources include: ammonia; ammonium salts of inorganic or organic acids such as ammonium chloride, ammonium sulfate, ammonium acetate, and ammonium phosphate; other nitrogen-containing compounds; peptone; meat extract; and corn steep liquor. Examples of inorganic substances include: monopotassium phosphate, dipotassium phosphate, magnesium phosphate, magnesium sulfate, sodium chloride, iron(I) sulfate, manganese sulfate, copper sulfate, and calcium carbonate. Usually, culture is carried out under aerobic conditions such as shaking culture or aeration agitation culture at 37° C. The pH is adjusted with an inorganic or organic acid, an alkali solution, or the like. During the culture, an antibiotic such as ampicillin or tetracycline may be added to the medium, if necessary.

When a microorganism transformed with an expression vector containing an inducible promoter is cultured, an inducer may be added to the medium, if necessary. For example, when a microorganism transformed with an expression vector containing a promoter that is inducible by isopropyl-β-D-thiogalactopyranoside (IPTG) is cultured, IPTG or the like may be added to the medium. When a microorganism transformed with an expression vector containing a trp promoter that is inducible by indoleacrylic acid (IAA) is cultured, IAA or the like may be added to the medium.

Examples of media for culturing a transgenic plant obtained from an animal host cell include common RPMI 1640 medium, DMEM medium, and a medium prepared by adding fetal bovine serum or the like to the aforementioned medium. Usually, culture is carried out in the presence of 5% $CO_2$ at 37° C. for 1 to 30 days. During the culture, an antibiotic such as kanamycin or penicillin may be added to the medium, if necessary.

If the protein of the present invention is produced in the relevant microorganism or cell after the culture, the protein of interest is extracted by disrupting the cultured microorganism or cell via ultrasonication, repeated freeze-thaw cycles, or processing with a homogenizer. If the protein of the present invention is secreted outside of the microorganism or cell, the culture fluid may be used in that state or subjected to centrifugation or another procedure to remove the microorganism or cell. Thereafter, conventional biochemical techniques for isolating/purifying a protein such as ammonium sulfate precipitation, gel chromatography, ion exchange chromatography, or affinity chromatography, are employed independently or in an appropriate combination to isolate and purify the protein of the present invention from the above culture product.

6. Method for Screening for a Substance that Regulates Plant Environmental Stress Tolerance The gene of the present invention can be used for screening for a substance that regulates plant environmental stress tolerance. As the expression level of the gene of the present invention in a plant or plant cell is elevated, the environmental stress tolerance of the plant is enhanced. As the expression level of the gene is lowered, however, environmental stress tolerance is deteriorated. Accordingly, a substance that regulates environmental stress tolerance can be screened for by employing an increase/decrease in the expression level of the gene of the present invention in a plant or plant cell as an indicator. More specifically, a candidate for a substance that regulates environmental stress tolerance is added to a plant that is capable of expressing the gene of the present invention, such as *Arabidopsis thaliana*, and changes in the expression level of the gene of the present invention in the plant cell are assayed via quantitative PCR, Northern blotting, or other means. If the expression level of the gene of the present invention is enhanced with the addition of the substance, this substance can be determined to be a candidate for a substance that enhances the environmental stress tolerance of the plant. If the expression level of the gene of the present invention is lowered with the addition of the substance, however, this substance can be determined to be a candidate for a substance that attenuates the environmental stress tolerance of the plant. Types of candidate substances to be screened for are not particularly limited. Examples thereof include: naturally occurring molecules, such as amino acid, peptide, oligopeptide, polypeptide, protein, and nucleic acid; lipid, steroid, glycopeptide, glycoprotein, and proteoglycan; a synthetic analogue of a naturally occurring molecule or a derivative thereof, such as a peptide mimic; non-naturally occurring molecules, such as a low molecular weight organic compound prepared via combinatorial chemistry or other techniques; and a mixture thereof.

Best Modes for Carrying Out the Invention

Hereafter, the present invention is described in greater detail with reference to the examples, although the technical scope of the present invention is not limited thereto.

EXAMPLE 1

Introduction of SRK2C Gene into Plant

There are 10 SnRK2 protein kinases (SRK2A to SRK2J) on the *Arabidopsis thaliana* genome, and they are classified into SnRK2a and SnRK2b subfamilies depending on phylogenetic systems (FIG. 1A). In the present example, full-length cDNA of SRK2C, which is a member of the SnRK2 protein kinase family, is isolated, this SRK2C gene is introduced into a cultured *Arabidopsis thaliana* cell to obtain a transgenic plant, and stress is applied to this transgenic plant to assay activation of SRK2C.

(1) Cloning of SRK2C Gene

Total RNA was extracted from an *Arabidopsis thaliana* seedling using the Total RNA Extraction Kit (Amersham). Total RNA was removed by digesting the genomic DNA with the use of the RNase free DNAse. The resultant was used as a template for cDNA synthesis, and oligo-dT was used as a primer to allow the SuperScript II reverse transcriptase (Invitrogen) to act, thereby synthesizing single-stranded cDNA. PCR was carried out using this single-stranded cDNA as a template, the sense primer 5'-TCTAGAATGGAGAGGTACGAAATAG-3' (SEQ ID NO: 3), and the antisense primer 5'-GGATCCCAAAGGG-GAAAGGAGATCAG-3' (SEQ ID NO: 4) to amplify cDNA of SRK2C. PCR was carried out under conditions of 98° C. for 2 minutes, 30 cycles of 95° C. for 30 seconds, 55° C. for 30 seconds, and 72° C. for 1 minute, and 74° C. for 5 minutes, followed by retention at 4° C. The length of the amplified fragment was approximately 1 kb, which was the intended length.

(2) Construction of Plasmid for Plant Transformation

The cDNA fragment of SRK2C obtained via RT-PCR was subcloned into the pGEM-T easy vector (Promega) and a large quantity of plasmid DNA was prepared using *E. coli* DH5α. This plasmid was processed with 2 types of restriction enzymes, i.e., BamHI and XbaI, to cleave the cDNA fragments of SRK2C, and the cleaved cDNA fragments were inserted into the BamHI and XbaI sites of the pBE2113 GFP vector to construct pBE2113:SRK2C-GFP.

(3) Transformation of *Arabidopsis thaliana* pBE2113:SRK2C-GFP and pBE2113GFP were introduced into *Agrobacterium* C58 by electroporation to obtain *Agrobacterium* for transformation. This *Agrobacterium* was transformed into the cultured *Arabidopsis thaliana* T87 cell and the *Arabidopsis thaliana* plant (Columbia) via vacuum infiltration. The transgenic plant was selected in a medium containing 30 mg/ml kanamycin and 100 mg/ml claforan, and expression of the introduced SRK2C-GFP was detected using a fluorescence detector (FLA 2000, Fuji Photo Film, Co., Ltd.). Thus, a plurality of SRK2C-GFP-overexpressing cell lines were obtained.

(4) Detection of SRK2C Protein Kinase Activity

Figure 2A:
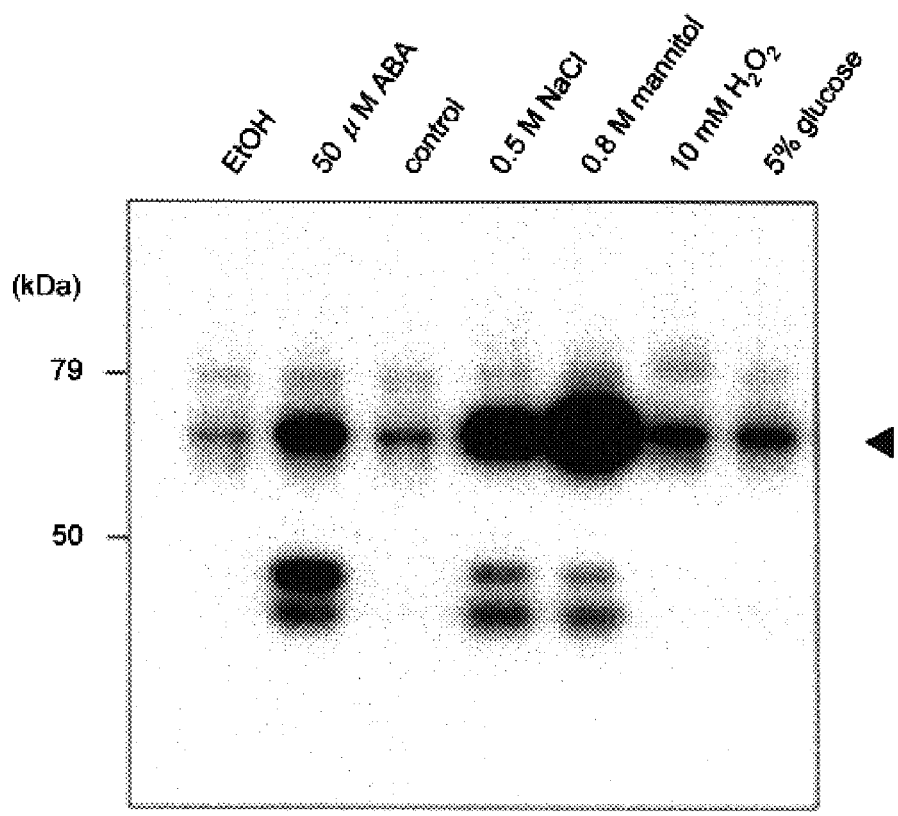
FIG. 2A shows the results of analyzing protein kinase activity of SRK2C after the application of hyperosmotic stress via an in-gel phosphorylation assay (the portion indicated by an arrow represents the relevant kinase activity).

The cultured SRK2C-GFP-overexpressing cells were treated with 50 μM abscisic acid (ABA), 0.5 M NaCl, 0.8 M mannitol, 10 mM $H_2O_2$, and a 5% glucose solution for 30 minutes each, immediately frozen with the aid of liquid nitrogen, and then stored at −80° C. Crude protein extracts were prepared from these cultured cells and fractionated to 10 μg each of crude protein fractions via the SDS-PAGE method. The polyacrylamide concentration in the gel to be used for SDS-PAGE was adjusted at 8%, and 5 mg/ml histone H3 (Sigma) was added. The gel after electrophoresis was washed two times with a washing buffer (composition: 25 mM Tris-Cl (pH 7.5), 1 mM DTT, 0.1 mM $Na_3VO_4$, 5 mM NaF, 0.5 mg/ml BSA, and 0.1% Triton X-100) for 30 minutes, placed in a renaturing buffer (composition: 25 mM Tris-Cl (pH 7.5), 1 mM DTT, 0.1 mM $Na_3VO_4$, and 5 mM NaF), and then incubated at 4° C. for 16 hours. The gel was soaked in a reaction buffer (composition: 25 mM HEPES, pH 7.5, 2 mM EGTA, 12 mM $MgCl_2$, 1 mM DTT, and 0.1 mM $Na_3VO_4$) for 30 minutes, 200 nM ATP and 50 μCi[γ-$^{32}$P]ATP (Perkin Elmer) were added, and the in-gel phosphorylation reaction was carried out at room temperature for 1 hour. After the reaction, the gel was washed with 5% trichloroacetic acid/1% sodium pyrophosphate, immobilized, and dehydrated using a gel dryer. Thereafter, radioactivity was detected via autoradiography. As a result, SRK2C was found to be activated by processing with 50 μM ABA, 0.5 M NaCl, and 0.8 M mannitol. Also, SRK2C was found to be particularly potently activated by processing with 0.5 M NaCl and 0.8 M mannitol (FIG. 2A).

Figure 2B:
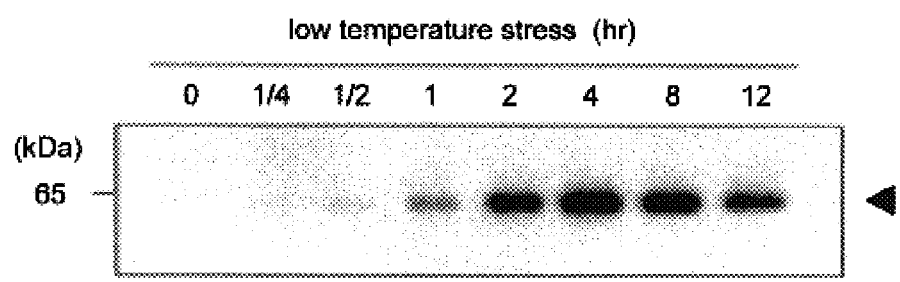
FIG. 2B shows the results of analyzing protein kinase activity of SRK2C after the application of low temperature stress via an in-gel phosphorylation assay (the portion indicated by an arrow represents the relevant kinase activity).

Also, SRK2C-GFP-overexpressing plants were subjected to low-temperature treatment in a refrigerator kept at 4° C. for a given period of time (0, ¼, ½, 1, 2, 4, 8, and 12 hours) and the kinase activity thereof was detected by the method mentioned above. Thus, SRK2C was found to be activated by low-temperature treatment (FIG. 2B).

EXAMPLE 2

Test of Dehydration Tolerance and Freezing Tolerance of SRK2C-GFP-overexpressing Plant The pBE2113GFP transgenic plants (vector control plants) and the SRK2C-GFP-overexpressing plants were allowed to grow for 4 weeks, water supply was suspended, and dehydration tolerance was tested. The survival ratio 14 days after the suspension of water supply was tested. As a result, the survival ratio of the SRK2C-GFP-overexpressing plants (lines #1 to 3) was found to be significantly higher than that of the vector control plants (VC). Thus, the SRK2C-GFP-overexpressing plants were found to have dehydration stress tolerance (FIG. 3A).

Also, similar plants were treated at −10° C. for 6 hours and the survival ratio thereof was tested. As a result, freezing tolerance of the SRK2C-GFP-overexpressing plants was found to have been significantly improved (FIG. 3B).

EXAMPLE 3

Expression Analysis of DREB/CBF Transcription Factor and the Group of Downstream Genes Thereof RNA was extracted from the SRK2C-overexpressing plants and from the vector control plants and fractionated to 10 μg each via electroporation in accordance with a conventional technique. The fractionated RNA was blotted onto a nylon membrane, hybridized to 32P-labeled RD29A, Cor15a, kin1, and AtGolS3-specific DNA probes, and washed under stringent conditions. Thereafter, radioactivity was detected via autoradiography.

Figure 4A:
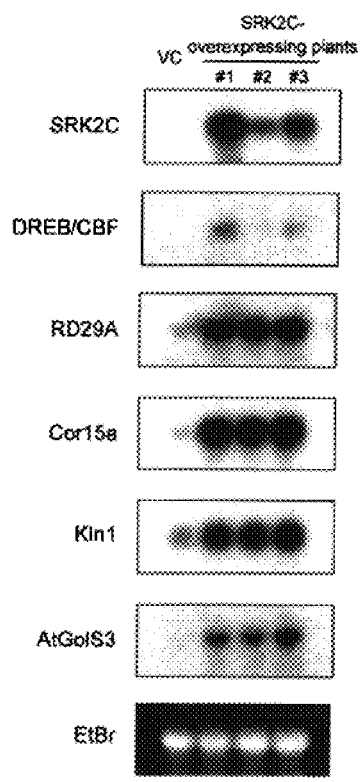
FIG. 4A shows the results of gene expression analysis of the SRK2C-overexpressing plants.

In the case of the SRK2C-overexpressing plants, expression levels of RD29A, Cor15a, kin1, AtGolS3, and the like, which were dehydration or low temperature stress-responsive genes, were found to be increased, and expression of the transcription factor DREB/CBF was found to be induced (FIG. 4A).

Figure 4B:
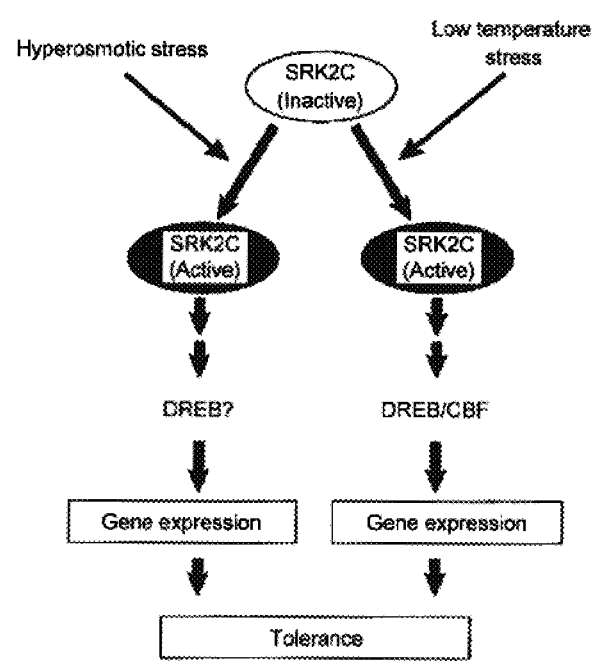
FIG. 4B is a model diagram showing the action mechanism of SRK2C.

An increase in the expression level of the DREB/CBF transcription factor in the SRK2C-overexpressing plants indicates that the increased level of RD29A expression or the like is affected by such transcription factor. Accordingly, SRK2C was considered to be a protein kinase that positively regulates the signal transduction system of plants' dehydration and low temperature stress responses. Also, improved stress tolerance of the SRK2C-overexpressing plants was considered to result from enhanced expression of the genes under the control of the DREB/CBF regulon (FIG. 4B).

All publications, patents, and patent applications cited herein are incorporated herein by reference in their entirety.

INDUSTRIAL APPLICABILITY

The present invention provides a transgenic plant that is highly tolerant to environmental stress, such as dehydration, osmotic, or low temperature stress. The environmental stress tolerance mechanism of the transgenic plant of the present invention is induced by the increased expression of the signal transduction factors located upstream of the gene group involved in environmental responses. Thus, the time period between stress application and tolerance acquirement is short. Since such signal transduction factor exhibits its functions when activated by environmental stress, its influence on plants is slight under normal growth conditions.

---

The invention claimed is:

1. A method for imparting stress tolerance to a transgenic plant comprising:

transforming a plant cell with a polynucleotide which encodes a polypeptide at least 95% homologous to SEQ ID NO: 2, wherein said polypeptide has kinase activity and which induces the expression of stress-responsive transcription factors, growing a transgenic plant tissue or plant from the transformed cell, selecting a transgenic plant tissue which has a phenotype of increased stress tolerance to dehydration, osmotic or low temperature stresses as compared to a plant tissue obtained from the corresponding untransformed plant cell and growing a plant from said tissue, or selecting a transgenic plant which has a phenotype of increased tolerance to dehydration, osmotic or low temperature stresses as compared to the corresponding untransformed plant.

2. The method of claim 1, wherein said transgenic plant or plant tissue is selected based on increased tolerance to dehydration.

3. The method of claim 1, wherein said transgenic plant or plant tissue is selected based on increased tolerance to osmotic stress.

4. The method of claim 1, wherein said transgenic plant or plant tissue is selected based on increased tolerance to low temperature.

5. The method of claim 1, wherein said polynucleotide encodes a polypeptide consisting of SEQ ID NO: 2.

6. The method of claim 1, wherein said polynucleotide comprises SEQ ID NO: 1.

7. The method of claim 1, wherein said polynucleotide encodes a polypeptide consisting of the amino acid sequence of SEQ ID NO: 2 except that 1 to 10 amino acid residues of the sequence of SEQ ID NO: 2 have been deleted or substituted with other amino acid residues, or in which 1 to 10 additional amino acid residues have been added to the sequence of SEQ ID NO: 2.

8. The method of claim 1, wherein said polynucleotide is at least 95% homologous to SEQ ID NO: 1.

9. The method of claim 1, wherein said polynucleotide comprises a selectable marker.

10. The method of claim 1, wherein said polynucleotide comprises a promoter.

11. The method of claim 1, wherein said polynucleotide comprises at least one enhancer, a terminator, a poly-A addition signal, and/or a 5'-UTR sequence.

12. The method of claim 1, wherein said polypeptide enhances the expression of a DREB/CBF transcription factor.

13. The method of claim 1, wherein said plant cell is monocotyledonous.

14. The method of claim 1, wherein said plant cell is dicotyledonous.

15. The method of claim 1, wherein said plant cell is selected from the group consisting of *Gramineae, Liliaceae, Zingiberaceae, Brassicaceae, Solanaceae, Leguminosae, Cucurbitaceae, Umbelliferae, Asteaceae, Malvaceae, Chenopodiaceae, Myrtaceae* and *Salicaceae*.

16. The method of claim 1, wherein said polynucleotide is inserted in a vector prior to transformation of said plant cell.

17. The method of claim 1, wherein said polynucleotide is inserted in an expression vector prior to transformation of said plant cell.

18. The method of claim 1, wherein said transgenic plant is transformed by *Agrobacterium*.

19. The method of claim 1, wherein said transgenic plant is produced by a PEG-calcium phosphate method.

20. The method of claim 1, wherein said transgenic plant is produced by electroporation, a liposome mediated method, a particle gun method or microinjection.

* * * * *